United States Patent [19]

Seuron et al.

[11] Patent Number: 5,166,358
[45] Date of Patent: Nov. 24, 1992

[54] PROCESS FOR 1-PHENYL-IMIDAZOLINE-2,5-DIONES

[75] Inventors: Patrick Seuron, St Cyr Au Mont d'Or; Daniel Varraillon, Reyrieux, both of France

[73] Assignee: Roussel Uclaf, Paris, France

[21] Appl. No.: 629,490

[22] Filed: Dec. 18, 1990

[30] Foreign Application Priority Data

Dec. 22, 1989 [FR] France .................. 89-17046

[51] Int. Cl.$^5$ .......................................... C07D 233/74
[52] U.S. Cl. .................................................. 548/321.1
[58] Field of Search ......................... 548/314; 564/405

[56] References Cited

U.S. PATENT DOCUMENTS

| | | | |
|---|---|---|---|
| 2,490,813 | 12/1949 | Hughes et al. | 564/405 |
| 3,914,311 | 10/1975 | Coulson | 564/405 |
| 4,036,850 | 7/1977 | Enders | 548/314 |
| 4,230,716 | 10/1980 | Jamieson et al. | 548/314 |
| 4,764,625 | 8/1988 | Turner et al. | 564/405 |
| 4,944,791 | 7/1990 | Schröder et al. | 548/314 |

OTHER PUBLICATIONS

Katritzky et al., The Principles of Heterocyclic Chemistry, pp. 157–158, Academic Press 1968.

Primary Examiner—Joseph Paul Brust
Assistant Examiner—MarySusan H. Gabilan
Attorney, Agent, or Firm—Bierman and Muserlian

[57] ABSTRACT

A process for the preparation of a compound of the formula

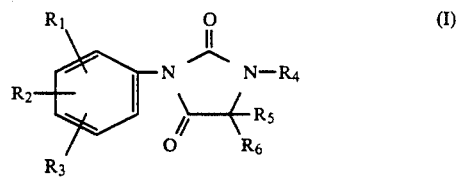

wherein $R_1$, $R_2$ and $R_3$ are individually selected from the group consisting of hydrogen, alkyl and alkoxy of 1 to 7 carbon atoms, alkenyl, alkynyl, alkenyloxy and alkynyloxy of 2 to 7 carbon atoms, phenyl, phenoxy, $-NO_2$, $-CF_3$, acyl of 1 to 7 carbon atoms and esterified carboxy and $R_4$, $R_5$ and $R_6$ are individually hydrogen or alkyl of 1 to 7 carbon atoms comprising reacting a compound of the formula

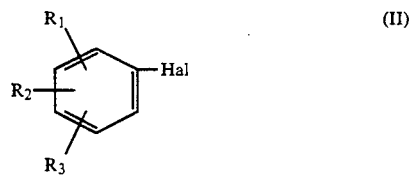

wherein $R_1$, $R_2$ and $R_3$ have the above definitions and Hal is halogen with a compound of the formula

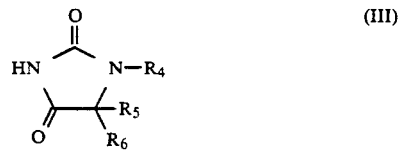

wherein $R_4$, $R_5$ and $R_6$ have the above definitions in the presence of a catalyst and optionally a solvent.

10 Claims, No Drawings

PROCESS FOR 1-PHENYL-IMIDAZOLINE-2,5-DIONES

OBJECTS OF THE INVENTION

It is an object of the invention to provide an improved process for the preparation of compounds of formula I.

This and other objects and advantages of the invention will become obvious from the following detailed description.

THE INVENTION

The novel process of the invention for the preparation of 1-phenyl-imidazoline-2,5-diones of the formula

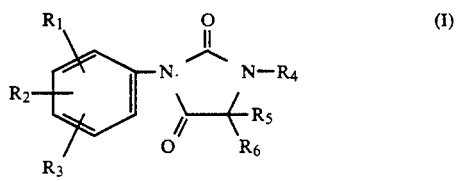

wherein $R_1$, $R_2$ and $R_3$ are individually selected from the group consisting of hydrogen, alkyl and alkoxy of 1 to 7 carbon atoms, alkenyl, alkynyl, alkenyloxy and alkynyloxy of 2 to 7 carbon atoms, phenyl, phenoxy, —$NO_2$, —$CF_3$, acyl of 1 to 7 carbon atoms and esterified carboxy and $R_4$, $R_5$ and $R_6$ are individually hydrogen or alkyl of 1 to 7 carbon atoms comprises reacting a compound of the formula

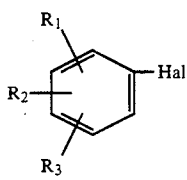

wherein $R_1$, $R_2$ and $R_3$ have the above definitions and Hal is halogen with a compound of the formula

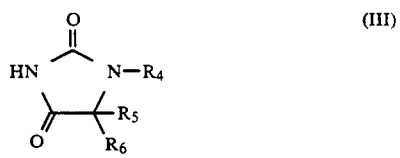

wherein $R_4$, $R_5$ and $R_6$ have the above definitions in the presence of a catalyst and optionally a solvent.

Examples of alkyl and alkoxy in the compounds of formula I are methyl, ethyl, n-propyl, isopropyl, n-butyl, isobutyl, sec.-butyl, t-butyl, n-pentyl, methoxy, ethoxy, isopropoxy, n-propoxy, n-butoxy, t-butoxy and n-pentyloxy. Examples of alkenyl and alkynyl are vinyl, allyl, 1-propenyl, butenyl, pentenyl, ethynyl, propargyl, butynyl and pentynyl. Examples of alkenyloxy or alkynyloxy are allyloxy, 1-butenyloxy, pentenyloxy, propargyloxy, butynyloxy and pentynyloxy.

The acyl of 1 to 7 carbon atoms may be —CO—Ra when Ra is alkyl of 1 to 6 carbon atoms or phenyl such as acetyl, propionyl, butyryl, benzoyl, valeroyl, hexanoyl, acryloyl, crotonoyl and carbamoyl. Esterified carboxy may be —COORb in which $R_b$ is alkyl of 1 to 6 carbon atoms such as methoxycarbonyl and ethoxycarbonyl or aryl such as benzyloxycarbonyl.

In a preferred mode of the process of the invention, one of $R_1$, $R_2$ and $R_3$ is hydrogen, one is 3-$CF_3$ and the other is 4-$NO_2$, $R_4$ is hydrogen and $R_5$ and $R_6$ are both methyl. This product is known as nilutamide generically and under the Trademark Anandron. The product is described in French Patent No. 2,329,276.

In the compounds of formula II, Hal is chlorine but may be bromine or iodine as well. The catalyst is believed to trap the hydrogen halide formed and to facilitate the condensation reaction of the compounds of formulae II and III.

The catalyst may be in the form of the metal per se or in the form of a metal oxide, or a metal salt or in the form of a base. In the preferred metal form the metal is copper or nickel. Examples of metal salts are chlorides or acetates. When the catalyst is in the form of a base, dimethylsulfoxide is preferably added to the reaction medium.

Preferably, the catalyst is copper, cuprous oxide, cupric oxide or a base such as sodium or potassium hydroxyde. If copper, is used, it is preferably in powdered form and the more preferred catalyst is cuprous oxide.

Examples of the optional solvent are high boiling ethers such as phenyl oxide, diglyme, triglyme and dimethylsulfoxide or a high boiling oil such as paraffin or vaseline. The ether type solvent is preferred, especially phenyl oxide or trigylme.

The condensation reaction can be effected at atmospheric pressure or under pressure and preferably at a high temperature, i.e. greater than 100° C. and preferably higher than 150° C. The reaction is usually effected for more than 2 hours.

In a preferred mode of the process of the invention, the compounds of formulae II and III are reacted in the presence of cuprous oxide in triglyme at 200° C. or more for more than 3 hours.

The compounds of formulae II and III are known compounds and are commercially available or made by known processes. For example, the compounds of formula II may be made by the processes described in Zhur. Preklad. Khim., Vol. 28, p. 969 to 975 (1955); CA, Vol. 50, p. 4881a, (1956); Tetrahedron, Vol. 43, p. 1753 (1987);

J. Org. Vol. 52, p. 2407 (1987);
Zh. Org. Khim; Vol. 21, p. 2006 (1985);
J. Fluor. Chem., Vol. 17, p. 345 (1981); and in German Patent No. DRp 637,318 (1935);
European Patent No. 0,130,875 and
Japanese Patent No. 81,121,524.

The products of formula III which are derivatives of hydantoin are widely used and are described for example in J. Pharm. Pharmacol., 67, Vol. 19(4), p. 209 to 216 (1967);

J. Chem. Soc., Vol. 74, (2), p. 219 to 221 (1972);
Khim. Farm. Zh., 67, Vol. 1 (5) p. 51 to 52;
German Patent No. 2,217,914;
European Patent No. 0,091,596; and
J. Chem Soc. Perkin. Trans. 1, Vol. 74 (2) p 48, p. 219-21.

In the following examples there are described several embodiments to illustrate the invention. However, it is to be understood that the invention is not intended to be limited to the specific embodiments.

EXAMPLE 1

1-(3'trifluoromethyl-4'-nitropheyl)-4,4-dimethyl-imidazoline-2,5-dione

The following were introduced into 383.52 ml of phenyl oxide: 225.60 grams of 2-nitro-5-chloro-trifluoromethylbenzene, described in the German Patent No. DRP 637,318, 128.10 grams of 5,5-dimethylhydantoin described in Beil., Vol. 24, 289 and 198.53 grams of cuprous oxide. The mixture was heated to 200° C. for 24 hours, then cooled to 20° C. and filtered. The residue was rinsed with phenyl oxide, then extracted with ethyl acetate. The ethyl acetate phase was concentrated to dryness under reduced pressure at 60° C. and the residue was taken up in ammoniacal dichloroethane. The crystals obtained were dried at 60° C. to obtain 66.55 grams of crude product which, after purification from aqueous ethanol yielded 62.55 grams of purified desired product.

EXAMPLE 2

1-(3'-trifluoromethyl-4'nitrophenyl)-4,4-dimethyl-imidazoline-2,5-dione

The following were introduced into 282 ml of triglyme: 112.8 grams of 2-nitro-5-chloro-trifluoromethylbenzene, 64.1 grams of 5,5-dimethyl-hydantoin and 33.5 grams of cuprous oxide. The mixture was heated to about 215° C.±5° C. for 4 hours, then cooled to 20° C. and filtered. The triglyme solution was recovered and a 22 Be ammonia solution (1V), toluene (1V) and demineralized water (4V) were added to the solution of triglyme (1V). The solution was stirred at 20° C. for 15 minutes, then cooled to about −10° C. and stirred again at −10° C. After washing and drying, 47.6 grams of the desired product were obtained.

EXAMPLE 3

1-(3-'trifluoromethyl-4'-nitrophenyl)-4,4-dimethyl-imidazoline-2,5-dione 30 ml of dimethylsulfoxide and 24.8 grams of 2-nitro-5-chloro trifluoromethylbenzene were introduced at 20° C. with stirring into 100 ml of dimethylsulfoxide, 12.80 grams of 5,5-dimethyl-hydantoin and 6.28 grams of potassium hydroxide in the form of flakes. The mixture was heated to 110° C. for a period of time variable between 3 and 18 hours. The product was characterized and determined by thin layer chromatography.

EXAMPLE 4

1-(3'-trifluoromethyl-4'-nitrophenyl)-4,4-dimethyl-imidazoline-2,5-dione 71.5 grams of copper in powder form were added to 96.10 grams of 5,5-dimethyl-hydantoin and 170.86 grams of 2-nitro-5-chloro trifluoromethylbenzene. The mixture was heated to 200° C. for about 21 hours, the pressure being maintained at 450 millibars, then, was cooled to 20° C. and taken up in 480 ml of ethanol. The product was characterized and determined by thin layer chromatography of the ethanol solution.

EXAMPLE 5

1-(3'-trifluoromethyl-4'-nitrophenyl)4,4-dimethyl-imidazoline-2,5-dione

The following were introduced into 288 ml of phenyl oxide: 96.10 grams of 5,5-dimethyl-hydantoin, 170.86 grams of 2-nitro-5-chloro trifluoromethylbenzene and 89.40 grams of cupric oxide. The mixture was heated to 190° C. for about 23 hours, then cooled to 20° C. and filtered. The residue was characterized in the phenyl oxide filtrate by thin layer chromatography.

The analytical results obtained for these 5 examples were identical to those obtained and indicated in French Patent No. 2,329,276.

Various modifications of the process of the invention may be made without departing from the spirit or scope thereof and it is to be understood that the invention is intended to be limited only as defined in the appended claims.

What we claim is:

1. A process for the preparation of a compound of the formula

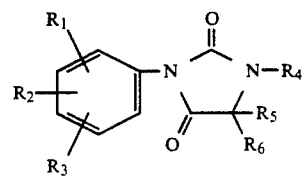

wherein $R_1$, $R_2$ and $R_3$ are individually selected from the group consisting of hydrogen, alkyl and alkoxy of 1 to 7 carbon atoms, alkenyl, alkynyl, alkenyloxy and alkynyloxy of 2 to 7 carbon atoms, phenyl, phenoxy, $-NO_2$, $-CF_3$, acyl of 1 to 7 carbon atoms and esterified carboxy and $R_4$, $R_5$ and $R_6$ are individually hydrogen or alkyl of 1 to 7 carbon atoms comprising reacting a compound of the formula

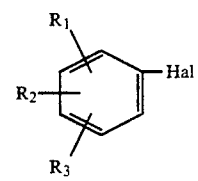

wherein $R_1$, $R_2$ and $R_3$ have the above definitions and Hal is halogen with a compound of the formula

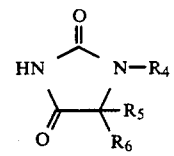

wherein $R_4$, $R_5$ and $R_6$ have the above definitions at a temperature greater than 100° C. and in the presence of a catalyst in the form of a metal per se or a metal in the form of an oxide or a salt and optionally a solvent.

2. The process of claim 1 wherein one of $R_1$, $R_2$ and $R_3$ is hydrogen and the other two are 3-$CF_3$ and 4-$NO_2$, $R_4$ is hydrogen and $R_5$ and $R_6$ are methyl.

3. The process of claim 1 wherein the catalyst is selected from the group consisting of copper, cuprous oxide and cupric oxide.

4. The process of claim 1 wherein the catalyst is cuprous oxide.

5. The process of claim 1 effected in an ether type solvent.

6. The process of claim 5 wherein the solvent is selected from the group consisting of phenyl oxide, diglyme, triglyme and dimethylsulfoxide.

7. The process of claim 5 wherein the solvent is phenyl oxide or triglyme.

8. The process of claim 1 wherein the reaction is effected at greater than 150° C.

9. The process of claim 1 wherein the reaction is effected for more than 2 hours.

10. The process of claim 1 wherein the catalyst is cuprous oxide and triglyme is the solvent and the reaction is effected at at least 200° C. for more than 3 hours.

* * * * *